United States Patent
Tanaka et al.

(10) Patent No.: US 6,472,540 B1
(45) Date of Patent: Oct. 29, 2002

(54) PROCESS FOR PRODUCING ε-CAPROLACTONE

(75) Inventors: Kazuo Tanaka; Atsushi Okoshi; Hiroshi Ogawa, all of Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/617,547

(22) Filed: Jul. 14, 2000

(30) Foreign Application Priority Data

Aug. 26, 1999 (JP) .......................................... 11-239636

(51) Int. Cl.⁷ ........................................... C07D 313/04
(52) U.S. Cl. ....................................................... 549/272
(58) Field of Search .......................................... 549/272

(56) References Cited

U.S. PATENT DOCUMENTS 5,994,565 A    11/1999   Tanaka et al.

FOREIGN PATENT DOCUMENTS

| EP | 972 771 A1 * | 7/1999 |
| JP | 11-158172 | 6/1999 |

\* cited by examiner

*Primary Examiner*—T. A. Solola
(74) *Attorney, Agent, or Firm*—Wenderoth, Lind & Ponack, LLP

(57) ABSTRACT

What is disclosed is a process for producing ε-caprolactone which comprises removing impurities by distillation from a reaction mixture obtained by co-oxidation of cyclohexanone and aldehyde, wherein ε-caprolactone separated from a purifying column is contacted with oxygen containing gas in the presence of cobalt. High boiling point components are removed to give an acid value of lower than 0.15 mgKOH/g. Thereby, a high quality ε-caprolactone providing improved polymer appearance is produced advantageously on an industrial scale without repeated purifying distillations or without using expensive stabilizer or adsorbent for the improvement of color.

13 Claims, No Drawings

PROCESS FOR PRODUCING ε-CAPROLACTONE

BACKGROUND OF THE INVENTION

1) Field of the invention

The present invention relates to a process for producing an ε-caprolactone which has excellent thermal coloring resistance and polycaprolactone which has low color.

2) Prior Art

ε-caprolactone is produced by oxidation of cyclohexanone. An oxidation method which uses an organic peroxyacid as oxidant and a co-oxidation method in which cyclohexanone is oxidized with an aldehyde are known. Peracetic acid or perpropionic acid is used as the organic peroxyacid in the oxidation method and acetaldehyde or benzaldehyde is used as the aldehyde in the co-oxidation method.

ε-caprolactone is polymerized and used for foaming materials, polyesterpolyols and biodegradable plastics etc. Improvement of ε-caprolactone quality is desired because high quality influences rate of polymerization and color of the product. In particular, purity, acid-value, water-content and thermal coloring resistance influence the color of the polymer and rate of polymerization Japanese Laid-open patent 11-158172 (1999) describes ε-caprolactone with less of a low boiling point component and high purity and having lower coloring at the stage of producing or storing of monomer and producing or using of polymers.

However, ε-caprolactone which has excellent thermal coloring resistance and polycaprolactone which has low color were not produced using ε-caprolactone having fewer low boiling point components and higher purity during co-xidation of cyclohexanone and aldehyde by our study because the low boiling point components in the co-oxidation method are different from those in the oxidation using peroxyacid.

SUMMARY OF THE INVENTION

It is an object of the present invention to provide a process for producing ε-caprolactone which has excellent thermal coloring resistance from co-oxidation of cyclohexanone and aldehyde, and to provide polycaprolactone which has low coloring.

The present inventors assiduously conducted investigations to solve the above problems, and found that (1) a small amount of high boiling point component which influences thermal coloring resistance and is difficult to separate is produced during co-oxidation of cyclohexanone and aldehyde, (2) the high boiling point component which influences thermal coloring resistance becomes possible to separate by introducing oxygen containing gas into the ε-caprolactone in the presence of cobalt, (3) ε-caprolactone which has excellent thermal coloring resistance is produced by introducing oxygen containing gas therein and removing low boiling point carboxylic acids, to obtain ε-caprolactone having acid values of lower than 0.15 mgKOH/g, (4) low color polycaprolactone is produced using this ε-caprolactone.

Thus, the present invention provides a process for producing ε-caprolactone by co-oxidation of cyclohexanone and an aldehyde to form a reaction mixture containing ε-caprolactone, low boiling components, high boiling components and color components, wherein the reaction mixture is subjected to an oxidation treatment with an oxygen containing gas in the presence of cobalt to convert color components to high boiling components and then separating the ε-caprolactone from the low and high boiling components, whereby the ε-caprolactone recovered has an acid value of less than 0.15 mg KOH/g.

DETAILED DESCRIPTION OF THE INVENTION

The aliphatic aldehyde used in the co-oxidation method may be acetaldehyde, propionaldehyde or butyraldehyde. The aromatic aldehyde generally used in the co-oxidation method may be benzaldehyde, tolualdehyde, dimethylbenzaldehyde, trimethylbenzaldehyde, ethylbenzaldehyde, cuminaldehyde, butylbenzaldehyde, methoxybenzaldehyde, phenoxybenzaldehyde, cyclohexylbenzaldehyde and biphenylaldehyde. When these aliphatic aldehydes or aromatic aldehydes possess isomeric forms, each isomer or the mixture thereof may be used.

Purified ε-caprolactone is produced by removing impurities from the reaction products of co-oxidation. When acetaldehyde is used as the aliphatic aldehyde, the reaction mixture contains ε-caprolactone, unreacted cyclohexanone, acetic acid, acetaldehyde, adipic acid, caprolactone oligomer, caprolactone polymer and oxycaproic acid etc. When 2,4-dimethylbenzaldehyde is used as the aromatic aldehyde, the reaction mixture contains ε-caprolactone, unreacted cyclohexanone, 2,4-dimethylbenzoic acid, 2,4-dimethylbenzaldehyde, adipic acid, caprolactone oligomer, caprolactone polymer and oxycaproic acid etc.

When acetaldehyde is used as the aliphatic aldehyde in distillation purification of the reaction mixture, the high boiling point component of by-product such as adipic acid) caprolactone oligomer, caprolactone polymer and oxycaproic acid is removed at first, then the low boiling point component such as unreacted cyclohexanone, acetic acid and acetaldehyde is removed. When 2,4-dimethylbenzaldehyde is used as the aldehyde, unreacted cyclohexanone (boiling point 155.6° C.) is separated at first, then the high boiling point component of 2,4-dimethylbenzoic acid (boiling point 267° C.), 2,4-dimethylbenzaldehyde (boiling point 225° C.) is removed. used as the aldehyde, unreacted cyclohexanone (boiling point 155.6° C.) is separated at first, then the high boiling point component of 2,4-dimethylbenzoic acid (boiling point 267° C.), 2,4-dimethylbenzaldehyde (boiling point 225° C.) is removed.

In the present invention, the reaction mixture from the oxidation product of cyclohexanone is purified by the above method. Then, the remaining high boiling point component is removed by distillation The ε-caprolactone thus obtained is purified by introducing oxygen containing gas in the presence of cobalt (which is referred as "oxidation treatment"), then changing the color component to a high boiling point component and removing a small amount of low boiling point acids by distillation to obtain the ε-caprolactone product (boiling point 235.3° C.).

These methods of distillation purification are performed by known methods at as low a temperature and as low a pressure as possible to avoid change in quality during distillation.

In the present invention, the temperature of the oxygen containing gas introduced to the ε-caprolactone separated by distillation, is in the range of 80–200° C., and preferably 100–180° C. . When the temperature is too low, a long time is required to change the color component, which is difficult to separate from ε-caprolactone, to a high boiling point component. When the temperature is too high, ε-caprolactone may be polymerized and may produce low boiling point aliphtic acids and increase the acid value.

In the present invention, the color component is changed to a high boiling point component by contacting ε-caprolactone with oxygen containing gas in the presence of cobalt. Decomposition of ε-caprolactone and generation of low boiling point carboxylic acid are restrained to decrease the acid value in the presence of cobalt.

Cobalt compounds which are soluble in ε-caprolactone such as cobalt naphtate or cobalt octylate are used in the oxidation treatment. The amount of cobalt added to ε-caprolactone is 0.001–10 ppm by weight, and preferably 0.01–5 ppm by weight. When the cobalt content is too low, decomposition of ε-caprolactone and generation of low boiling point carboxylic acids are increased which decreases the acid value, and colored polycaprolactone is produced when ε-caprolactone thus oxidation treated is polymerized. When cobalt content is too high, ε-caprolactone is apt to polymerize spontaneously.

Generally, air is used for the oxygen containing gas and the pressure of the reaction is from one atmosphere to 10 kg/cm2. Oxygen containing gas is introduced continuously and ε-caprolactone accompanied by vent gas is recovered by condensation. The pressure of oxygen introduced to the ε-caprolactone is 0.0002–1.0 kg/cm2, and preferably 0.0005–0.1 kg/cm2. Oxygen pressure in the contacting tank is calculated from the concentration of oxygen in vent gas from the condenser. When the oxygen pressure is too high, decomposition of ε-caprolactone and generation of low boiling point carboxylic acids are increased, increasing acid value. When the oxygen pressure is too low, the problem of thermal coloring resistance may tend to occur because the conversion of coloring components to high boiling point component is decreased.

The mol-ratio of oxygen to ε-caprolactone is in the range of 0.0001–0.030. The amount of oxygen used is controlled to keep the acid value within 0.3 mgKOH/g by oxidation treatment when ε-caprolactone is decomposed to low boiling point carboxylic acids. The time of the oxidation treatment is from 5 minutes to 10 hours and preferably from 15 minutes to 7 hours.

By contact of ε-caprolactone with oxygen containing gas in the presence of cobalt according to the above method, the coloring component which is present in a significant amount in ε-caprolactone is changed to a high boiling point component. Formation of by product low boiling point carboxylic acids that cause coloring of the polymer is decreased. Components that cause coloring become high boiling point components which are separated easily by simple distillation or general distillation because the difference of boiling point between ε-caprolactone and the component is large. ε-caprolactone which is separated from the purification column is contacted with oxygen containing gas because large amounts of coloring component are produced by this treatment when ε-caprolactone contains a large amount of impurity.

Though low boiling point carboxylic acid is produced when the coloring component is oxidized to form a high boiling point component, the acid value of ε-caprolactone for oxidation treatment should be lower than 5 mgKOH/g. This ε-caprolactone is distilled again if necessary. As low boiling point carboxylic acids such as acetic acid, propionic acid, butyric acid and pentanoic acid possess large differences in boiling point; these low boiling point carboxylic acid are separated by simple distillation or purification distillation with reflux if necessary.

After ε-caprolactone is separated from the distillation column with introduction of oxygen containing gas, coloring components are removed by re-distillation and excellent thermal color resistant ε-caprolactone is obtained. Low color polycaprolactone is produced from this ε-caprolactone.

Though these treatments may be carried out batch-wise, semi-continuously or continuously, continuous method is preferable.

Polycaprolactone is used in many fields industrially according to the average molecular weight and functional groups contained. For example, polycaprolactone of a molecular weight of 500–5000 with glycol as starter is used as a raw material for polyurethane and paint. Polycaprolactone containing a double bond suitable for radical polymerization is used for coating materials for car and home electric products. Polycaprolactones possessing molecular weights of over 10000 are used for plastic forming products, film and hot melting adhesives. These polycaprolactones are mainly produced by polymerization using compounds containing hydroxy-functional groups as polymerization starters.

Compounds containing active hydrogen except water, such as ethylene glycol, propylene glycol, 1,4-butanediol, 1,3-butylenediol, diethylene glycol, neopentyl glycol, 1,6-hexanediol, trimethyrolpropane, and pentaerythritol are used as polymerization starting materials to produce polycaprolactone.

The kind and amount of the starter is decided by use of polycaprolactone resin.

For the catalyst to produce polycaprolactone, general catalysts for ring opening, adduct or polymerization reactions may be used. Concretely inorganic bases, inorganic acids, organic bases metal catalysts, tin compounds, titanium compounds, aluminum compounds, zinc compounds, molybdenum compounds and zirconium compounds are used. Among them, from the standpoint of handling, harmlessness, reactivity, colorlessness and stability; tin compounds or titanium compounds are preferable. As the tin compound of the present invention, a monobutyl tin compound such as tin(l)octyl acid, monobutyl tin oxide, monobutyl tin tri(2-ethylhexanate); dibutyl tin compounds such as dibutyl tin oxide, diisobutyl tin oxide, dibutyl tin acetate, di-n-butyl tin di-laurate; and titanium compound such as tetramethyl-titanate, tetraethyl-titanate, tetra-n-propyltitanate, tetraisopropyl-titanate, and tetrabutyl-titanate are used. These compounds may be used independently or as mixtures.

The temperature of polymerization to produce polycaprolactone is 50–250° C., preferably 90–220° C., and more preferably 100–200° C . When the temperature is lower than 50° C., the rate of polymerization to polycaprolactone is too low. When the temperature is higher than 250° C., polycaprolactone may decompose causing coloring and producing byproducts.

For the polymerization reactor of polycaprolactone, known reactors such as batch reactors with impellers, continuous or semi-continuous reactors, kneader type mixers, screw type mixers, static mixer type reactors and reactors connected to them continuously may be used.

The water content of ε-caprolactone for polymerization is 0.5% or less by weight, preferably 0.1% or less by weight, and more preferably 0.03% or less by weight. Dilute solution or stabilizers may be used in the polymerization of ε-caprolactone in the present invention.

According to this invention, as disclosed in the following Examples, by removing high boiling point components by distillation from ε-caprolactone separated from the purifying column after introduction of oxygen containing gas in the presence of cobalt, ε-caprolactone which has excellent thermal coloring resistance is obtained. From ε-caprolactone obtained by the present invention, polycaprolactone which has low coloring may be produced and high quality of polycaprolactone product may be obtained.

PREFERRED EMBODIMENTS OF THE INVENTION

Some o f the preferred embodiments of the present invention will be explained in more detail by referring to Examples, which are not intended to limit the scope of the present invention.

In the following Examples and Comparative Examples, % and ppm are weight based. The following items are measured by these methods.
(1) Acid value: Calculated by amount of 1/10N KOH per ε-caprolactone 1 g by titration to neutralize .
(2) Water content: Measured by a Karl Fisher type water content analyzer.
(3) Color test of heated ε-caprolactone: 30 ml of ε-caprolactone is measured in a glass test tube (10 mmID, 160 mmL) and heated to 150° C. for one hour, then compared with an APHA standard solution by eye.
(4) Color of polycaprolactone: 30 ml of polycaprolactone is measured in a glass test tube (20 mmID, 160 mmL) and heated to 80° C., then compared with an APHA standard solution by eye.

PRODUCTION EXAMPLE 1

A liquid mixture containing 80 wt % of cyclohexanone, 20 wt % of 2,4-dimethylbenzaldehyde and 1 ppm (as cobalt) of cobalt naphtate as catalyst was fed at the rate of 3000 g/hr into a flow pass type autoclave having an interior capacity of 6L, provided with a stirrer. The continuous reaction was conducted at a reaction temperature of 35° C. under a pressure of 25 kg/cm$^2$G while adjusting the air charge to reduce the oxygen concentration in the off gas to 10 vol % and the reaction mixture was drawn out continuously to maintain a constant liquid level.

The amount of the reaction mixture drawn at a steady state was 3086 g/h. The components of the reaction mixture were ε-caprolactone 7.92%, 2,4-dimethylbenzoic acid 12.75%, 2,4-dimethylbenzaldehyde 7.58%, cyclohexanone 70.60% and other components 1.15%. The hold-up time of the reaction mixture was 0.97 hour and conversion of the 2,4-dimethylbenzaldehyde was 61.0%.

From the reaction mixture thus obtained, cyclohexanone was separated by a film evaporator, and then 2,4-dimethylbenzoic acid and other higher boiling components and cyclohexanone remainded. Unreacted 2,4-dimethylbenzaldehyde and the other lower boiling components were removed by distillation. Then the higher boiling components were removed by purifying distillation. The obtained distillate of ε-caprolactone (purity; 99.93%, acid value: 0.05 mgKOH/g, water content: 130 ppm, thermal coloring resistance: 60APHA) was used for the following Examples and Comparative Examples.

150 g of ε-caprolactone obtained in Production Example 1, 5 g of ethylene glycol and 0.2 g of dibutyltinoxide as catalyst were fed to an autoclave, then reacted at 170° C. for 2 hours under a flow of nitrogen gas. The color of polycaprolactone obtained was 60APHA.

COMPARATIVE EXAMPLE 1

ε-caprolactone obtained in Production Example 1 was distilled using a theoretical 30 stage distillation column at a reflux ratio of 2.3 to distill 95% of feed amount. The quality of the product in purity: 99.94%, acid value: 0.04 mgKOH/g, water content: 120 ppm and result of thermal coloring resistance was 50APHA. The quality of the product is not improved enough without oxidation treatment.

150 g of product ε-caprolactone, 5 g of ethylene glycol and 0.2 g of dibutyltinoxide as catalyst were fed to an autoclave, then reacted at 170° C. for 2 hours under a flow of nitrogen gas. The color of polycaprolactone obtained was 50APHA.

COMPARATIVE EXAMPLE 2

4.5 kg of ε-caprolactone obtained in the Production Example 1 was charged to an 8L vessel, and heated to 145° C., then ε-caprolactone was fed at a rate of 3 kg/hr; 5% oxygen containing gas was fed at 1.05 NL/hr and product was drawn out continuously to maintain constant liquid level. This oxidation treated ε-caprolactone was simply distilled continuously. The product of the distillation had a purity of 99.91%, acid value: 0.19 mgKOH/g, water content: 120 ppm and result of thermal coloring resistance was 15 APHA.

This ε-caprolactone was polymerized by the same methods as were used in Production Example 1. The color of polycaprolactone obtained was 40APHA. The result of the thermal coloring resistance was improved from Comparative Example 1, however, the color of polycaprolactone was not improved enough because the acid value rose too high.

EXAMPLE 1

Comparative Example 2 repeated using ε-caprolactone added to 0.05 ppm of cobalt using the ε-caprolactone obtained in Production Example 1. The product of the distillation had a purity of 99.92%, acid value: 0.12 mgKOH/g, water content: 130 ppm and the result of thermal coloring resistance was 15APHA. This ε-caprolactone was polymerized by the same methods as Production Example 1. The color of polycaprolactone obtained was 25APHA. The result of thermal coloring resistance and the color of polycaprolactone were improved from Comparative Example 1 by the oxygen treatment using cobalt catalyst.

EXAMPLE 2

The ε-caprolactone of Comparative Example 2 was treated with oxygen and was distilled at 25 torr and a reflux ratio of 2.3 using a theoretical 30 stage distillation column. The product of the distillation had a purity of 99.94%, acid value: 0.04 mgKOH/g, water content: 120 ppm and the result of the thermal coloring resistance was 10APHA. This ε-caprolactone, was polymerized by the same methods as were used in Production Example 1. The color of the polycaprolactone obtained was 25APHA.

EXAMPLE 3

150 g of ε-caprolactone obtained in Example 1, 5 g of ethylene glycol and 0.8 mg of tin chloride as catalyst were charged to a reactor and then reacted at 150° C. for 3 hours under a flow of nitrogen. Residual ε-caprolactone was less than 1%, and the color of the polycaprolactone obtained was 25APHA.

EXAMPLE 4

150 g of ε-caprolactone obtained in Example 1, 5 g of ethylene glycol and 1.5 mg of titanium tetrabutyloxide as catalyst were charged to a reactor, then reacted at 170° C. for 3 hours under a flow of nitrogen. Residual ε-caprolactone was less than 1%, and the color of the polycaprolactone obtained was 25APHA.

EXAMPLE 5

150 g of ε-caprolactone obtained in Example 1, 171 g of hydroxyethylmethacrylate and 16 mg of monobutyl tin oxide as catalyst were charged to a reactor and then reacted at 100° C. for 15 hours under a flow of nitrogen. Residual ε-caprolactone was less than 1%, and the color of the polycaprolactone obtained was 25APHA.

What is claimed is:

1. In a process for producing ε-caprolactone by co-oxidation of cyclohexanone and an aldehyde to form a reaction mixture containing ε-caprolactone, low boiling components, high boiling components and color components, the improvement which comprises subjecting the reaction mixture to an oxidation treatment with an oxygen containing gas in the presence of cobalt to convert color components to high boiling components and then recovering the ε-caprolactone having an acid value of less than 0.15 mg KOH/g.

2. The process according to claim 1 wherein the amount of cobalt is 0.001–10 ppm by weight of ε-caprolactone.

3. The process according to claim 1 wherein the amount of cobalt is 0.01–5 ppm by weight of ε-caprolactone.

4. The process according to claim 1 wherein the pressure of the oxygen contacting the ε-caprolactone is 0.0002–1.0 kg/cm$^2$.

5. The process according to claim 1 wherein the pressure of the oxygen contacting the ε-caprolactone is 0.0005–0.1 kg/cm$^2$.

6. The process according to claim 1 wherein the molar ratio of oxygen to ε-caprolactone is 0.0001–0.030.

7. The process according to claim 1 wherein the time of oxidation treatment is from 5 minutes to 10 hours.

8. The process according to claim 1 wherein the time of oxidation treatment is from 15 minutes to 7 hours.

9. The process according to claim 1 wherein the treatment is batch-wise.

10. The process according to claim 1 wherein the treatment is continuous.

11. The process according to claim 1 wherein the oxidation treatment is preformed at 80–200° C.

12. The process according to claim 1 wherein the oxidation treatment is preformed at 100–180° C.

13. The process according to claim 1 wherein the low boiling and high boiling components are separated from ε-caprolactone by distillation.

* * * * *